United States Patent
Govari

(10) Patent No.: US 7,549,960 B2
(45) Date of Patent: *Jun. 23, 2009

(54) IMPLANTABLE AND INSERTABLE PASSIVE TAGS

(75) Inventor: Assaf Govari, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 440 days.

This patent is subject to a terminal disclaimer.

(21) Appl. No.: 10/029,595

(22) Filed: Dec. 21, 2001

(65) Prior Publication Data

US 2002/0107445 A1    Aug. 8, 2002

Related U.S. Application Data

(63) Continuation-in-part of application No. 09/265,715, filed on Mar. 11, 1999.

(51) Int. Cl.
*A61B 8/00* (2006.01)
(52) U.S. Cl. .............. 600/437; 600/443; 600/444; 600/445; 600/446; 600/447
(58) Field of Classification Search ........ 600/407, 600/424, 429, 447, 437, 300, 562, 443, 444, 600/445, 446; 340/870.28; 324/207.17, 324/67, 207.12; 382/124; 606/1, 32; 604/65
See application file for complete search history.

(56) References Cited

U.S. PATENT DOCUMENTS

| | | | |
|---|---|---|---|
| 3,644,825 A | 2/1972 | Davis, Jr. et al. | 324/41 |
| 3,713,133 A | 1/1973 | Nathans | 340/280 |
| 3,868,565 A | 2/1975 | Kuipers | 324/34 R |
| 4,017,858 A | 4/1977 | Kuipers | 343/100 R |
| 4,054,881 A | 10/1977 | Raab | 343/112 R |
| 4,173,228 A | 11/1979 | Van Steenwyk et al. | |
| 4,317,078 A | 2/1982 | Weed et al. | 324/208 |
| 4,407,296 A | 10/1983 | Anderson | |

(Continued)

FOREIGN PATENT DOCUMENTS

DE    30 11 671 A1    10/1981

(Continued)

OTHER PUBLICATIONS

U.S. Appl. No. 09/265,715, Biosense, Inc.

(Continued)

*Primary Examiner*—Brian Casler
*Assistant Examiner*—Baisakhi Roy
(74) *Attorney, Agent, or Firm*—Louis J. Capezzuto

(57) ABSTRACT

Apparatus for determining the position of an object within a body of a subject includes at least one acoustic wave generator, adapted to direct a first acoustic wave toward the body at a first frequency. An acoustic tag is adapted to be fixed to the object, the tag including a shell defining a cavity therein and a medium contained within the shell, such that responsive to incidence thereon of the first acoustic wave, the tag emits a second acoustic wave at a second frequency, different from the first frequency. One or more detectors are adapted to detect the second acoustic wave and to generate signals responsive thereto. A signal processor is coupled to process the signals so as to determine coordinates of the object in the body.

37 Claims, 3 Drawing Sheets

U.S. PATENT DOCUMENTS

| | | | |
|---|---|---|---|
| 4,485,813 A | 12/1984 | Anderson et al. | |
| 4,560,930 A | 12/1985 | Kouno | 324/207 |
| 4,613,866 A | 9/1986 | Blood | 343/448 |
| 4,642,786 A | 2/1987 | Hansen | 364/559 |
| 4,651,436 A | 3/1987 | Gaal | 33/533 |
| 4,710,708 A | 12/1987 | Rorden et al. | 324/207 |
| 4,807,202 A | 2/1989 | Cherri et al. | 367/129 |
| 4,815,469 A | 3/1989 | Cohen et al. | |
| 4,846,191 A | 7/1989 | Brockway et al. | |
| 4,849,692 A | 7/1989 | Blood | 324/208 |
| 4,905,698 A | 3/1990 | Strohl, Jr. et al. | 128/653 R |
| 4,917,095 A | 4/1990 | Fry et al. | 128/660.03 |
| 4,945,305 A | 7/1990 | Blood | 324/207.17 |
| 4,967,755 A | 11/1990 | Pondorf et al. | |
| 5,002,137 A | 3/1991 | Dickinson et al. | 175/19 |
| 5,042,486 A | 8/1991 | Pfeiler et al. | 128/653 R |
| 5,057,095 A | 10/1991 | Fabian | |
| 5,068,608 A | 11/1991 | Clark, Jr. | 324/220 |
| 5,078,144 A | 1/1992 | Sekino et al. | 128/660.03 |
| 5,099,845 A | 3/1992 | Besz et al. | 128/653.1 |
| 5,172,056 A | 12/1992 | Voisin | 324/207.17 |
| 5,201,715 A | 4/1993 | Masters | |
| 5,211,165 A | 5/1993 | Dumoulin et al. | 128/653.1 |
| 5,215,680 A | 6/1993 | D'Arrigo | 252/307 |
| 5,251,635 A | 10/1993 | Dumoulin et al. | 128/653.1 |
| 5,253,647 A | 10/1993 | Takahashi et al. | 128/653.1 |
| 5,255,680 A | 10/1993 | Darrow et al. | 128/653.1 |
| 5,265,610 A | 11/1993 | Darrow et al. | 128/653.1 |
| 5,269,289 A | 12/1993 | Takehana et al. | 128/4 |
| 5,273,025 A | 12/1993 | Sakiyama et al. | 128/6 |
| 5,275,166 A | 1/1994 | Vaitekunas et al. | 128/660.03 |
| 5,295,486 A | 3/1994 | Wollschlager et al. | 128/661.01 |
| 5,309,913 A | 5/1994 | Kormos et al. | 128/653.1 |
| 5,325,873 A | 7/1994 | Hirschi et al. | 128/899 |
| 5,330,520 A | 7/1994 | Maddison et al. | |
| 5,353,354 A * | 10/1994 | Keller et al. | 382/128 |
| 5,353,800 A | 10/1994 | Pohndorf et al. | |
| 5,375,596 A | 12/1994 | Twiss et al. | 128/653.1 |
| 5,377,678 A | 1/1995 | Dumoulin et al. | 128/653.1 |
| 5,383,874 A | 1/1995 | Jackson et al. | 606/1 |
| 5,391,199 A | 2/1995 | Ben-Haim et al. | 607/122 |
| 5,404,877 A | 4/1995 | Nolan et al. | |
| 5,412,619 A | 5/1995 | Bauer | 367/128 |
| 5,425,367 A | 6/1995 | Shapiro et al. | 128/653.1 |
| 5,425,382 A | 6/1995 | Golden et al. | 128/899 |
| 5,429,132 A | 7/1995 | Guy et al. | 128/653.1 |
| 5,437,277 A * | 8/1995 | Dumoulin et al. | 600/424 |
| 5,443,489 A | 8/1995 | Ben-Haim | 607/115 |
| 5,453,687 A | 9/1995 | Zierdt et al. | 324/207.17 |
| 5,456,718 A | 10/1995 | Szymaitis | |
| 5,471,988 A | 12/1995 | Fujio et al. | 128/660.03 |
| 5,513,636 A | 5/1996 | Palti | |
| 5,522,869 A | 6/1996 | Burdette et al. | 607/97 |
| 5,549,638 A | 8/1996 | Burdette | 607/97 |
| 5,558,091 A | 9/1996 | Acker et al. | 128/653.1 |
| 5,558,092 A | 9/1996 | Unger et al. | 128/660.03 |
| 5,566,676 A | 10/1996 | Rosenfeldt et al. | |
| 5,577,502 A | 11/1996 | Darrow et al. | 128/653.1 |
| 5,617,857 A | 4/1997 | Chader et al. | 128/653.1 |
| 5,622,169 A | 4/1997 | Golden et al. | 128/653.1 |
| 5,636,644 A | 6/1997 | Hart et al. | |
| 5,645,065 A | 7/1997 | Shapiro et al. | |
| 5,682,886 A | 11/1997 | Delp et al. | 128/653.1 |
| 5,689,576 A * | 11/1997 | Schneider et al. | 382/124 |
| 5,690,113 A | 11/1997 | Sliwa, Jr. et al. | |
| 5,694,945 A | 12/1997 | Ben-Haim | 128/736 |
| 5,697,377 A | 12/1997 | Wittkampf | 128/696 |
| 5,715,822 A | 2/1998 | Watkins et al. | 128/653.5 |
| 5,727,552 A | 3/1998 | Ryan | |
| 5,729,129 A | 3/1998 | Acker et al. | 324/207.12 |
| 5,743,267 A | 4/1998 | Nikolic et al. | |
| 5,752,513 A | 5/1998 | Acker et al. | 128/653.1 |
| 5,762,066 A * | 6/1998 | Law et al. | 600/439 |
| 5,762,609 A | 6/1998 | Benaron et al. | |
| 5,769,843 A | 6/1998 | Abela et al. | 606/10 |
| 5,797,849 A | 8/1998 | Vesely et al. | 600/461 |
| 5,798,693 A | 8/1998 | Engellenner | |
| 5,817,022 A | 10/1998 | Vesely | |
| 5,868,673 A * | 2/1999 | Vesely | 600/407 |
| 5,913,820 A | 6/1999 | Bladen et al. | |
| 5,928,137 A | 7/1999 | Green | |
| 5,964,709 A * | 10/1999 | Chiang et al. | 600/447 |
| 5,999,857 A | 12/1999 | Weijand et al. | |
| 6,021,352 A | 2/2000 | Christopherson et al. | |
| 6,026,818 A | 2/2000 | Blair et al. | |
| 6,053,873 A | 4/2000 | Govari et al. | |
| 6,073,043 A * | 6/2000 | Schneider | 600/424 |
| 6,076,007 A | 6/2000 | England et al. | |
| 6,140,740 A | 10/2000 | Porat et al. | |
| 6,141,293 A * | 10/2000 | Amorai-Moriya et al. | 367/127 |
| 6,159,156 A | 12/2000 | Van Bockel | |
| 6,161,032 A | 12/2000 | Acker | |
| 6,172,499 B1 | 1/2001 | Ashe | |
| 6,198,963 B1 | 3/2001 | Haim et al. | |
| 6,206,835 B1 | 3/2001 | Spillman, Jr. et al. | |
| 6,223,066 B1 * | 4/2001 | Govari | 600/424 |
| 6,226,547 B1 * | 5/2001 | Lockhart et al. | 600/424 |
| 6,237,398 B1 | 5/2001 | Porat et al. | |
| 6,239,724 B1 * | 5/2001 | Doron et al. | 340/870.28 |
| 6,270,458 B1 | 8/2001 | Barnea | |
| 6,305,381 B1 | 10/2001 | Weijand et al. | |
| 6,332,089 B1 * | 12/2001 | Acker et al. | 600/424 |
| 6,347,241 B2 * | 2/2002 | Burbank et al. | 600/431 |
| 6,373,240 B1 * | 4/2002 | Govari | 324/207.17 |
| 6,380,732 B1 * | 4/2002 | Gilboa | 324/207.17 |
| 6,490,474 B1 * | 12/2002 | Willis et al. | 600/424 |
| 6,638,231 B2 | 10/2003 | Govari et al. | |
| 6,788,967 B2 * | 9/2004 | Ben-Haim et al. | 600/424 |
| 6,875,179 B2 | 4/2005 | Ferguson et al. | |
| 7,160,258 B2 * | 1/2007 | Imran et al. | 600/593 |
| 7,174,201 B2 * | 2/2007 | Govari et al. | 600/424 |
| 2001/0018594 A1 | 8/2001 | Krag | |
| 2001/0051766 A1 * | 12/2001 | Gazdzinski | 600/309 |
| 2002/0107445 A1 | 8/2002 | Govari | |
| 2003/0023161 A1 | 1/2003 | Govari et al. | |
| 2003/0120150 A1 | 6/2003 | Govari | |
| 2004/0015075 A1 | 1/2004 | Kimchy et al. | |
| 2004/0015079 A1 | 1/2004 | Berger et al. | |

FOREIGN PATENT DOCUMENTS

| | | |
|---|---|---|
| DE | 100 03 338 A | 11/2000 |
| EP | 0 021 451 A1 | 7/1981 |
| EP | 0 053 976 A2 | 6/1982 |
| EP | 0 646 365 A1 | 4/1995 |
| EP | 0 897 690 A1 | 2/1999 |
| EP | 1 004 267 A2 | 5/2000 |
| EP | 1 034 738 A | 9/2000 |
| JP | 60-70324 A | 4/1985 |
| JP | H08-015489 B2 | 2/1996 |
| JP | 08-313622 | 11/1996 |
| WO | WO 83 02053 A | 6/1983 |
| WO | WO 83/03348 A1 | 10/1983 |
| WO | WO 92/03090 | 3/1992 |
| WO | WO 94/04938 | 3/1994 |
| WO | WO 94/23647 | 10/1994 |
| WO | WO 96/05768 | 2/1996 |
| WO | WO 96/05768 A1 | 2/1996 |
| WO | WO 96/41119 | 12/1996 |
| WO | WO 97/29678 | 8/1997 |
| WO | WO 97/29701 | 8/1997 |
| WO | WO 97/29709 | 8/1997 |
| WO | WO 97/29710 | 8/1997 |
| WO | WO 97/32179 | 9/1997 |

| | | |
|---|---|---|
| WO | WO 97/33513 A1 | 9/1997 |
| WO | WO 98/11840 | 3/1998 |
| WO | WO 98/36236 | 8/1998 |
| WO | WO 99 27837 A | 6/1999 |
| WO | WO 99/34453 | 7/1999 |
| WO | WO 99/34453 A1 | 7/1999 |
| WO | WO 99/34731 A1 | 7/1999 |
| WO | WO 99 51143 A | 10/1999 |
| WO | WO 00/16686 A2 | 3/2000 |
| WO | WO 00/16686 A3 | 3/2000 |
| WO | WO 00/32092 A1 | 6/2000 |
| WO | WO 01/36014 A2 | 5/2001 |
| WO | WO 01 64109 A | 9/2001 |
| WO | WO 02 39917 A | 5/2002 |

OTHER PUBLICATIONS

EPO Search Report dated Oct. 13, 2003 for EPO Application No. EP 03 25 3785.

EPO Search Report dated Dec. 4, 2003 for EPO Application No. EP 02 25 8960.

EPO Search Report dated Oct. 14, 2003 for EPO Application No. EP 03 25 3786.

EPO Search Report dated Oct. 13, 2003 for EPO Application No. EP 03 25 3784.

Weir, R.F. et al.: "A Portable, Real-Time, Clinical Gait Velocity Analysis System", IEEE Transactions on Rehabilitation Engineering, US, NY, vol. 5 No. 4 p. 310-320, Dec. 1997.

European Search Report EP 01 31 0521 dated Mar. 19, 2002.

Dargie, Henry J. "Diagnosis and Management of Heart Failure", BMJ 1994;308:321-8.

Stevenson, LW & Perloff, JK "The Limited Reliability of Physical Signs for Estimating Hemodynamics in Chronic Heart Failure", JAMA 1989;261, No. 6:884-888.

Chakko S et al. "Clinical, Radiographic, and Hemodynamic Correlations in Chronic Congestive Heart Failure: Conflicting Results May Lead to Inappropriate Care", AJM 1991;90:353-359.

Stevenson LW "Tailored Therapy Before Transplantation for Treatment of Advanced Heart Failure: Effective Use of Vasodilators and Diuretics", J Heart Lung Transplant 1991;10:468-76.

Stevenson LW et al. "Poor Survival of Patients with Idopathic Cardiomyopathy Considered Too Well for Transplantation", AJM 1987; 83:871-876.

Steinhaus David M et al. "Initial Experience with an Implantable Hemodynamic Monitor", Circulation 1996;93No. 4:745-752.

Ohlsson A et al. "Continuous Ambulatory Haemodynamic Monitoring with an Implantable System", European Heart Journal 1998;19:174-184.

Biosense, Inc. U.S. Appl. No. 10/029,473.

* cited by examiner

IMPLANTABLE AND INSERTABLE PASSIVE TAGS

CROSS-REFERENCE TO RELATED APPLICATIONS

This application is a continuation-in-part of U.S. patent application Ser. No. 09/265,715, filed Mar. 11, 1999, which is incorporated herein by reference.

FIELD OF THE INVENTION

The present invention relates generally to position sensing systems, and specifically to systems for determining the position of an object inside a human body.

BACKGROUND OF THE INVENTION

In many medical procedures, probes, such as endoscopes and catheters, are temporarily inserted into a patient's body. There are also procedures in which devices, such as implants, are inserted into the body permanently or for extended periods. Various methods of determining the location of these inserted medical devices are known in the art. X-ray imaging is the most commonly used location confirmation system. Position sensing systems can also be used for this purpose, and are preferable in particular when the location of the device must be tracked over an extended period.

Ultrasound intrabody position sensing is well known. Such systems commonly require an active transducer in the device that is inserted into the body, connected by wires to a console outside the body. The transducer either receives ultrasonic waves from emitters outside the body or radiates ultrasonic waves to receivers outside the body. Other ultrasonic systems use a passive ultrasound reflector in the inserted device which gives a strong reflection of ultrasonic waves irradiating the body without the necessity of running wires through the catheter. These passive systems necessarily create a strong background of ultrasonic radiation against which the position of the reflector must be found.

Other position sensing systems use electromagnetic fields. For example, PCT Patent Publication WO 96/05768 to Ben-Haim et al., whose disclosure is incorporated herein by reference, describes a locating system for determining the location and orientation of an invasive medical instrument whereby an externally applied RF field induces a current in three coils located within the invasive medical instrument. Wires or some other form of physical leads are required to carry this induced signal from the catheter to a signal processor in the extrabody space. The processor analyzes the signal so as to calculate the location and orientation of the invasive medical instrument.

In many applications, it is advantageous to fix a wireless passive emitter, or "tag," to the device that is inserted into the body. Such a tag contains no internal power source, but is rather actuated by an external energy field, typically applied from outside the body. The tag then emits ultrasonic or electromagnetic energy, which is detected by antennas or other sensors outside the body. The detected signals are generally used to simply to ascertain the presence of the tag within a given region (such as the abdominal cavity), although some tags may also be used to determine position coordinates. Passive ultrasonic reflectors, mentioned above, are one simple example of such tags. Other passive tags receive and re-emit electromagnetic radiation, typically with a frequency and/or phase shift. Hybrid tags, combining ultrasonic and electromagnetic interactions, are also known in the art.

For example, U.S. Pat. No. 6,026,818 to Blair et al., whose disclosure is incorporated herein by reference, describes a method and device for the detection of unwanted objects in surgical sites, based on a medically inert detection tag which is affixed to objects such as medical sponges or other items used in body cavities during surgery. The detection tag contains a single signal emitter, such as a miniature ferrite rod and coil and capacitor element embedded therein. Alternatively, the tag includes a flexible thread composed of a single loop wire and capacitor element. A detection device is utilized to locate the tag by pulsed emission of a wide-band transmission signal. The tag resonates with a radiated signal, in response to the wide-band transmission, at its own single non-predetermined frequency, within the wide-band range. The return signals build up in intensity at a single (though not pre-defined) detectable frequency over ambient noise, so as to provide recognizable detection signals.

U.S. Pat. No. 5,057,095 to Fabian, whose disclosure is incorporated herein by reference, describes apparatus for detecting a surgical implement in human or animal tissue, comprising a detector responsive to the presence, within an interrogation zone, of a surgical implement to which a marker is secured. The marker is adapted to produce identifying signal characteristics within a frequency band generated in the interrogation zone. Variations in the phase and or direction of the interrogating field and changes in the electromagnetic coupling between markers and receiver are intended to optimize coupling therebetween.

U.S. Pat. No. 6,076,007 to England et al., whose disclosure is incorporated herein by reference, describes a method for determining the position and orientation of a surgical device within a human body. In one application, a catheter or prosthesis is characterized in that it carries, at a predetermined location, a tag formed of a high permeability, low coercivity magnetic material. The position of the tag (and hence of the surgical device) is sensed by remotely detecting its magnetic response to an interrogating signal.

U.S. Pat. No. 5,325,873 to Hirschi et al., whose disclosure is incorporated herein by reference, describes a system to verify the location of a tube or other object inserted into the body. It incorporates a resonant electrical circuit attached to the object which resonates upon stimulation by a hand-held RF transmitter/receiver external to the body. The electromagnetic field generated due to resonance of the circuit is detected by the hand-held device, which subsequently turns on a series of LEDs to indicate to the user the direction to the target. An additional visual display indicates when the transmitter/receiver is directly above the object.

In a non-medical context, U.S. Pat. No. 3,713,133 to Nathans et al., whose disclosure is incorporated herein by reference, describes a theft-prevention system in which a piezoelectric crystal having a resonant frequency is incorporated into a device which is then attached to individual items within a store. When a radio frequency (RF) signal having a frequency equal to the resonant frequency of the crystal strikes the crystal, an oscillating electrical field gradient is produced across the face of the crystal at the radiated RF frequency, and two tin foil members mounted on the crystal vibrate, emitting ultrasound. Detection of the ultrasound under appropriate conditions produces an alarm, indicative of an attempt to remove the item from the store without authorization. In another embodiment, a small, thin metal diaphragm vibrates when irradiated with an ultrasound field at or near the resonant frequency. The vibration of the diaphragm induced by the ultrasound field modulates an incident RF field, and the modulation is detected by an RF transducer to activate the alarm. These systems do not provide specific information describing the location of the item, but only that the item has entered a detection area (typically near an exit from the store).

Passive sensors and transponders, fixed to implanted devices, can also be used for conveying other diagnostic information to receivers outside the body. For example, U.S. Pat. No. 6,053,873 to Govari et al., whose disclosure is incorporated herein by reference, describes a stent adapted for measuring a fluid flow in the body of a subject. The stent contains a coil, which receives energy from an electromagnetic field irradiating the body so as to power a transmitter for transmitting a pressure-dependent signal to a receiver outside the body. In one embodiment, the transmitter is based on a tunnel diode oscillator circuit, suitably biased so as to operate in a negative resistance regime, as is known in the art.

As another example, U.S. Pat. No. 6,206,835 to Spillman et al., whose disclosure is incorporated herein by reference, describes an implant device that includes an integral, electrically-passive sensing circuit, communicating with an external interrogation circuit. The sensing circuit includes an inductive element and has a frequency-dependent variable impedance loading effect on the interrogation circuit, varying in relation to the sensed parameter.

SUMMARY OF THE INVENTION

It is an object of the present invention to provide improved wireless tags, which are fixed to devices that are inserted into or implanted in the body of a patient for use in determining coordinates of the device inside the body.

It is a particular object of some aspects of the present invention to provide tags that enable both position and orientation coordinates of the device inside the body to be determined accurately.

In some preferred embodiments of the present invention, a wireless tag comprises an ultrasonic reflector or transducer, having a nonlinear and/or anisotropic response to incident ultrasonic radiation. The ultrasonic radiation is directed toward the area of the tag by one acoustic radiators outside the body. In one of these embodiments, the radiation reflected from the tag is shifted in frequency, so that acoustic detectors outside the body can distinguish the reflected signal easily from the background radiation generated by the acoustic radiators. In some of these preferred embodiments, the tag is not spherically symmetrical, causing the intensity and, preferably, the frequency shift of the reflected radiation to vary as a function of angle. The differences in the frequency spectrum of the reflected signal detected at the different positions of the acoustic detectors can then be used to determine not only the position, but also the orientation, of the tag, and hence of the device to which the tag is attached.

In other preferred embodiments in which ultrasonic irradiation is used, the tag comprises a piezoelectric or magnetoacoustic transducer, having an anisotropic response to the incident ultrasonic radiation. In response to the ultrasonic irradiation, the transducer emits electromagnetic radiation, which is detected by antennas or other electrical sensors outside the body. The spatial variations of the detected radiation are analyzed to determine the position and orientation of the tag. In the piezoelectric case, the piezoelectric crystal is preferably fabricated and polarized so that its voltage response to the ultrasonic radiation is anisotropic. Different resonant circuits are coupled across different faces of the crystal so that the frequency of the emitted radiation varies as a function of angle relative to the axis of the crystal. In the magnetoacoustic case, the transducer preferably comprises a magnetostrictive material, which is shaped asymmetrically so as to have different resonant vibrational frequencies along different axes. The magnetic field generated by the transducer will thus also have a frequency that varies as a function of angle.

In still other preferred embodiments of the present invention, the tag comprises a transducer, which emits ultrasonic radiation in response to electromagnetic radiation directed toward the tag from outside the body. Some tags of this type are described in the above-mentioned U.S. patent application Ser. No. 09/265,715. Another tag of this type comprises a magnetoacoustic transducer, which is excited by the incident electromagnetic field to vibrate at a characteristic resonant vibrational frequency. As described above, the transducer is preferably shaped so that the frequency varies as a function of angle. The emitted ultrasonic radiation is detected by acoustic sensors outside the body, and its spatial variations are analyzed to determine the position and orientation of the tab. A piezoelectric transducer may be used in like fashion.

There is therefore provided, in accordance with a preferred embodiment of the present invention, apparatus for determining the position of an object within a body of a subject, including:

at least one acoustic wave generator, adapted to direct a first acoustic wave toward the body at a first frequency;

an acoustic tag adapted to be fixed to the object, the tag including a shell defining a cavity therein and a medium contained within the shell, such that responsive to incidence thereon of the first acoustic wave, the tag emits a second acoustic wave at a second frequency, different from the first frequency;

one or more detectors, adapted to detect the second acoustic wave and to generate signals responsive thereto; and a signal processor, coupled to process the signals so as to determine coordinates of the object in the body.

Preferably, there is substantially no wired connection to the tag.

In a preferred embodiment, the tag has an axis and is constructed so that responsive to incidence thereon of the first acoustic wave, the tag emits the second acoustic wave at the second frequency with a first pattern of intensity variation relative to the axis, and a third acoustic wave at a third frequency, different from the first and second frequencies, with a second pattern of intensity variation relative to the axis, and responsive to detection of the second and third acoustic waves by the one or more detectors, the signal processor is adapted to determine an angular orientation of the object responsive to a difference between the first and second patterns.

There is also provided, in accordance with a preferred embodiment of the present invention, apparatus for determining the position of an object within a body of a subject, including:

at least one acoustic wave generator, adapted to direct acoustic waves toward the body over a range of frequencies, including at least first and second frequencies;

an acoustic tag adapted to be fixed to the object, the tag being constructed so as to reflect the acoustic waves at the first frequency with a first spatial pattern of intensity variation, and to reflect the acoustic waves at the second frequency with a second spatial pattern of intensity variation;

one or more detectors, adapted to detect the reflected acoustic waves and to generate signals responsive thereto; and a signal processor, coupled to process the signals so as to determine an angular orientation coordinate of the object in the body responsive to a difference between the first and second spatial patterns.

Preferably, the signal processor is further adapted to determine position coordinates of the object responsive to the signals.

Further preferably, the tag has an axis, and the tag is constructed so that in the first spatial pattern, the acoustic waves are reflected predominantly in a first direction relative to the axis, while in the second spatial pattern, the acoustic waves are reflected predominantly in a second direction relative to the axis, different from the first direction.

There is additionally provided, in accordance with a preferred embodiment of the present invention, apparatus for determining the position of an object within a body of a subject, including:

at least one acoustic wave generator, adapted to direct acoustic waves toward the body;

a transducer adapted to be fixed to the object and constructed to emit electromagnetic radiation responsive to the acoustic waves with a response that varies depending on an orientation angle of the transducer relative to the at least one acoustic wave generator;

one or more detectors, adapted to detect the electromagnetic radiation emitted by the transducer and to generate signals responsive thereto; and a signal processor, coupled to process the signals so as to determine an angular orientation coordinate of the object in the body.

In a preferred embodiment, the transducer includes a piezoelectric crystal, which is polarized so as to respond anisotropically to the acoustic waves. Preferably, the piezoelectric crystal has multiple opposing faces, and the transducer further includes a plurality of resonant circuit elements having different, respective resonant frequencies, the circuit elements being coupled between respective pairs of the faces of the crystal so as to emit the electromagnetic radiation at the different resonant frequencies with respective amplitudes that vary responsive to the orientation angle of the transducer. Most preferably, the circuit elements include coils having different, respective values of inductance.

In another preferred embodiment, the transducer includes a magnetostrictive element, which is shaped so as to respond anisotropically to the acoustic waves. Preferably, the magnetostrictive element is shaped to as to focus the electromagnetic radiation that it emits.

There is further provided, in accordance with a preferred embodiment of the present invention, apparatus for determining the position of an object within a body of a subject, including:

at least one field generator, adapted to generate an electromagnetic field within the body;

a transducer adapted to be fixed to the object and constructed to emit acoustic waves responsive to the electromagnetic field;

one or more acoustic detectors, adapted to detect the acoustic waves emitted by the transducer and to generate signals responsive thereto; and a signal processor, coupled to process the signals so as to determine coordinates of the object in the body.

In a preferred embodiment, the transducer includes a magnetoacoustic transducer, preferably including a magnetostrictive material. Preferably, the magnetoacoustic transducer is shaped so as to respond anisotropically to the electromagnetic field, so that the acoustic waves emitted thereby vary as a function of an orientation angle of the transducer relative to the at least one field generator, and the signal processor is adapted to determine the orientation angle of the object responsive to the signals. Most preferably, the magnetoacoustic element is shaped to as to focus the electromagnetic radiation that it emits.

There is moreover provided, in accordance with a preferred embodiment of the present invention, a method for determining the position of an object within a body of a subject, including:

fixing an acoustic tag to the object, the tag including a shell defining a cavity therein and a medium contained within the shell, such that responsive to incidence thereon of a first acoustic wave at a first frequency, the tag emits a second acoustic wave at a second frequency, different from the first frequency;

inserting the object into the body of the subject;

directing the first acoustic wave toward the body at the first frequency, causing the tag to emit the second acoustic wave at the second frequency;

detecting the second acoustic wave and generating signals responsive thereto; and processing the signals so as to determine coordinates of the object in the body.

There is furthermore provided, in accordance with a preferred embodiment of the present invention, a method for determining the position of an object within a body of a subject, including:

fixing an acoustic tag to the object, the tag being constructed so as to reflect acoustic waves at a first frequency with a first spatial pattern of intensity variation, and to reflect acoustic waves at a second frequency with a second spatial pattern of intensity variation;

inserting the object into the body of the subject;

directing the acoustic waves toward the body over a range of frequencies, including at least the first and second frequencies;

detecting the reflected acoustic waves and generating signals responsive thereto; and processing the signals so as to determine an angular orientation coordinate of the object in the body responsive to a difference between the first and second spatial patterns.

There is also provided, in accordance with a preferred embodiment of the present invention, a method for determining the position of an object within a body of a subject, including:

fixing a transducer to the object, the transducer being configured to emit electromagnetic radiation responsive to acoustic waves incident thereon with a response that varies depending on an orientation angle of the transducer relative to a source of the acoustic waves;

inserting the object into the body of the subject;

directing the acoustic waves toward the body;

detecting the electromagnetic radiation emitted by the transducer responsive to the acoustic waves, and generating signals responsive thereto; and processing the signals so as to determine an angular orientation coordinate of the object in the body.

There is additionally provided, in accordance with a preferred embodiment of the present invention, a method for determining the position of an object within a body of a subject, including:

fixing a transducer to the object, the transducer being configured to emit acoustic waves responsive to an electromagnetic field that is incident thereon;

inserting the object into the body of the subject;

generating the electromagnetic field within the body;

detecting the acoustic waves emitted by the transducer and generating signals responsive thereto; and processing the signals so as to determine coordinates of the object in the body.

The present invention will be more fully understood from the following detailed description of the preferred embodiments thereof, taken together with the drawings in which:

DETAILED DESCRIPTION OF PREFERRED EMBODIMENTS

Figure 1:
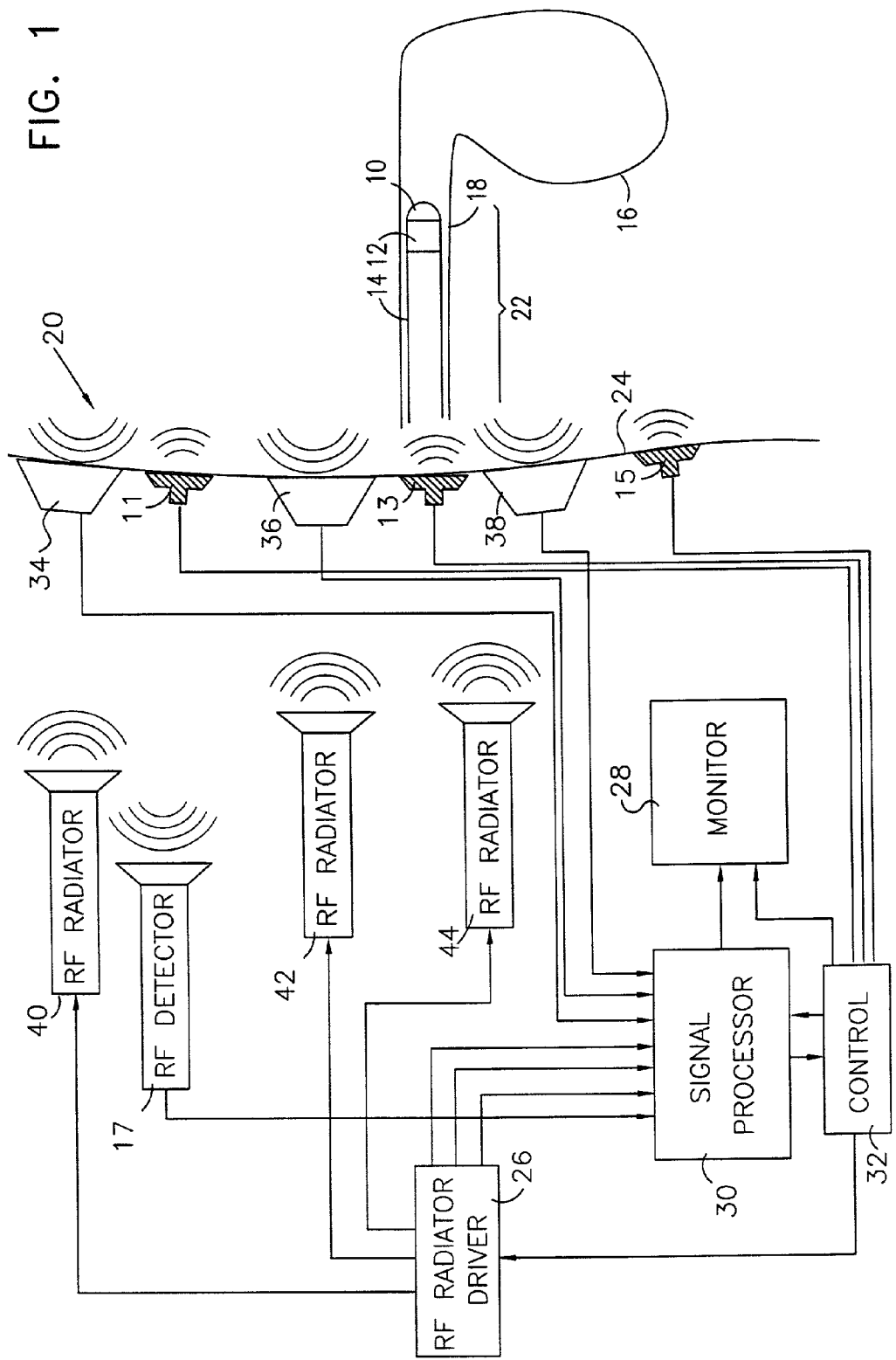
FIG. 1 is a schematic illustration of a catheter tracking system, in accordance with a preferred embodiment of the present invention.

FIG. 1 is a schematic representation of a system 20 for tracking the position of a catheter 22 in the body of a human or non-human subject, in accordance with a preferred embodiment of the present invention. In this application, catheter 22 is inserted through a blood vessel 18 of a patient using standard techniques. Catheter 22 comprises a body 14, a wireless locating tag 12, and an active portion 10 at the distal end of the catheter. The active portion may include, for example, an electrical sensor, an ultrasound head, a fiber optic viewing head, an electrical stimulator, an electrical or laser ablator, an ionic sensor, an oxygen or carbon dioxide sensor, an accelerometer, a blood pressure or temperature sensor, or a cryogenic probe, as are known in the art. In general, the catheter will include leads, light guides, wave guides, etc., for energizing the active portion in response to commands of an operator, and may also include a tip deflection mechanism, for steering the catheter inside the body.

The position and/or orientation of the distal end of the catheter is obtained by determining the position and/or orientation of tag 12. Different possible implementations of tag 12 are shown below in FIGS. 2, 3, 4 and 5A/5B and are described in detail with reference thereto. In some embodiments, tag 12 emits ultrasonic radiation when subjected to ultrasonic irradiation by acoustic generators 11, 13 and 15. The ultrasonic emission of the tag is sensed by acoustic detectors 34, 36 and 38. The acoustic generators and detectors typically comprise ultrasound transducers, as are known in the art, and it is possible to use the same transducers from both irradiation and detection.

In alternative embodiments, tag 12 emits electromagnetic radiation when subjected to the ultrasonic irradiation, and this electromagnetic emission is detected by at least one radio frequency (RF) detector 17. In still other embodiments, tag 12 emits ultrasonic radiation when subjected to electromagnetic irradiation by RF radiators 40, 42 and 44. The RF radiators and detectors preferably comprise coils, or antennas of other types, as are known in the art.

For convenience and compactness of illustration, FIG. 1 shows the entire gamut of irradiators—including both acoustic generators 11, 13 and 15, and RF radiators 40, 42 and 44—as well as showing both acoustic detectors 34, 36 and 38 and RF detector 17. In practice, only one type of irradiator and one type of detector are typically used in any given embodiment, depending on the type of tag 12 that is used. Acoustic generators 11, 13 and 15 and acoustic detectors 34, 36 and 38 are preferably positioned against a body surface 24 of the patient, as is known in the art, while the RF radiators and detector may be positioned a short distance away from surface 24.

The RF or acoustic irradiation of the area of tag 12 is initiated by control signals from a control unit 32. When RF irradiation is used, these control signals cause an RF radiator driver 26 to generate driving signals to RF radiators 40, 42 and 44. A representation of the driving signals to the RF radiators or acoustic generators is also sent to a signal processor 30. The RF or acoustic detectors are arranged such that signal processor 30 can utilize inputs representing the driving signals and measurements from the detectors in order to calculate the position and orientation of locating transducer 12. The position measurement is preferably based on a triangulation algorithm, as is known in the art. The detectors may be arranged in any convenient position and orientation, but it is preferable that (a) they are fixed in respect to some reference frame; (b) they are non-overlapping, that is, there are no two detectors with the exact, identical location and orientation; (c) the detectors are not placed collinearly; and (d) two detectors and the locating transducer are at no time all collinear.

The numbers and positions of the different type of irradiators and detectors shown in the figure are chosen for illustration only, and greater or lesser numbers of each item may be used, depending on specific application requirements. In practice, the active end of the catheter may be used to gather information, such as ultrasound echo information, electrical activity information, etc., and optionally to perform certain procedures on the arteries (or veins) or other tissue within an organ chamber 16 to which the artery (or vein) leads. Particular examples of organ chambers are the chambers of the heart, brain, or gastrointestinal tract. Depending on the application, system 20 may be configured to provide precise knowledge of the orientation of catheter 22 (e.g., for laser ablation in the heart), or to provide only knowledge of the position of the catheter or other probe (e.g., for gastrointestinal tract tube placement). Although the embodiment of FIG. 1 shows specifically the use of tag 12 in intravascular catheter 22, the tags shown and described hereinbelow may likewise be used in medical probes of other types, as well as in implantable devices.

In response to the ultrasonic or electromagnetic radiation emitted by tag 12, acoustic detectors 34, 36, and 38 or RF detector 17 produce electrical signals which are passed to signal processor 30, in either analog or digital form. Signal processor 30 processes the outputs of the detectors to calculate the position and/or orientation of tag 12, and transmits this information to a display monitor 28 and/or control unit 32. Methods of calculating the coordinates of catheter 22 using system 20 are described in detail in the above-mentioned patent application Ser. No. 09/265,715.

Figure 2:
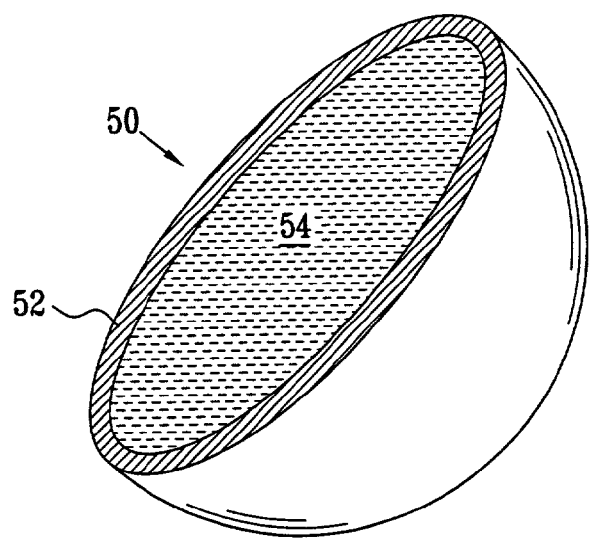
FIG. 2 is a schematic pictorial illustration showing a cutaway view of an ultrasonic reflector, in accordance with a preferred embodiment of the present invention.

FIG. 2 is a schematic, pictorial, partly cutaway illustration of an ultrasonic reflecting tag 50, in accordance with a preferred embodiment of the present invention. Tag 50 comprises a shell 52 that is struck by ultrasound waves generated by one or more of acoustic generators 11, 13, 15 outside the patient's body The incident waves induce the tag to resonate and to emit a detectable ultrasound echo. If shell 52 is spherical (as shown), then the emitted echo is generally isotropic, and triangulation of the echo yields the location of the target in the body.

Preferably, shell 52 contains a medium 54, and the shell and medium are configured so that tag 50 has a nonlinear vibrational response to incident ultrasonic radiation. Ultrasound waves having a frequency f1, emitted by the acoustic generators outside the patient's body, strike the shell, imparting energy to the shell and/or the contained medium. The shell then emits ultrasound waves at its resonant frequency f2, which is different from f1. The resonant frequency is determined by parameters such as the shell radius, Young modulus and thickness, as is known in the art. The power of the signal emitted by the tag at frequency f2 is preferably measured by detectors 34, 36, 38 at three or more sites outside the patient's body, in order to allow the determination of the target's location by triangulation. Preferably, the material of shell 52 is selected so as to be clearly visible using standard imaging techniques.

Figure 3:
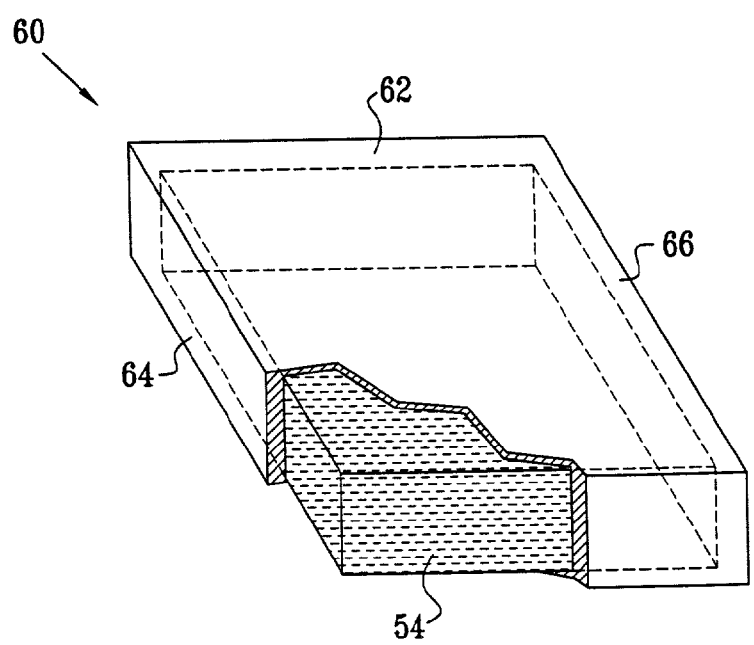
FIG. 3 is a schematic pictorial illustration showing another ultrasonic reflector, in partial cutaway view, in accordance with a preferred embodiment of the present invention.

FIG. 3 is a schematic, pictorial, partly cutaway view of a tag 60, which reflects incident ultrasound waves, in accordance with another preferred embodiment of the present invention. As in the preceding embodiment, tag 60 comprises a shell containing medium 54. In this case, however, the tag has the form of a rectangular prism with unequal faces 62, 64 and 66, making up the shell. Alternatively, the tag may be cylindrical or have some other non-spherical shape. Because of the asymmetry of tag 60, the ultrasound radiation emitted by tag 60 is typically anisotropic. If multiple acoustic generators 11, 13 and 15 are used in alternation to irradiate tag 60 from different angles, and detectors 34, 36 and 38 then measure the strength of the reflected waves at these different angles, signal processor 30 can determine both the position and orientation coordinates of the tag inside the patient's body. As noted earlier, methods of calculation for this purpose are described in the above-mentioned patent application Ser. No. 09/265,715.

Furthermore, because of the differing dimensions of faces 62, 64 and 66, each axis of tag 60 typically has its own characteristic resonant frequency or frequency shift. As a result, the reflected ultrasound waves received by detectors 34, 36 and 38 vary as a function of detector position and orientation not only in intensity, but also in frequency shift. The frequency shifts are preferably measured and used in determining the orientation angle of the tag.

Figure 4:
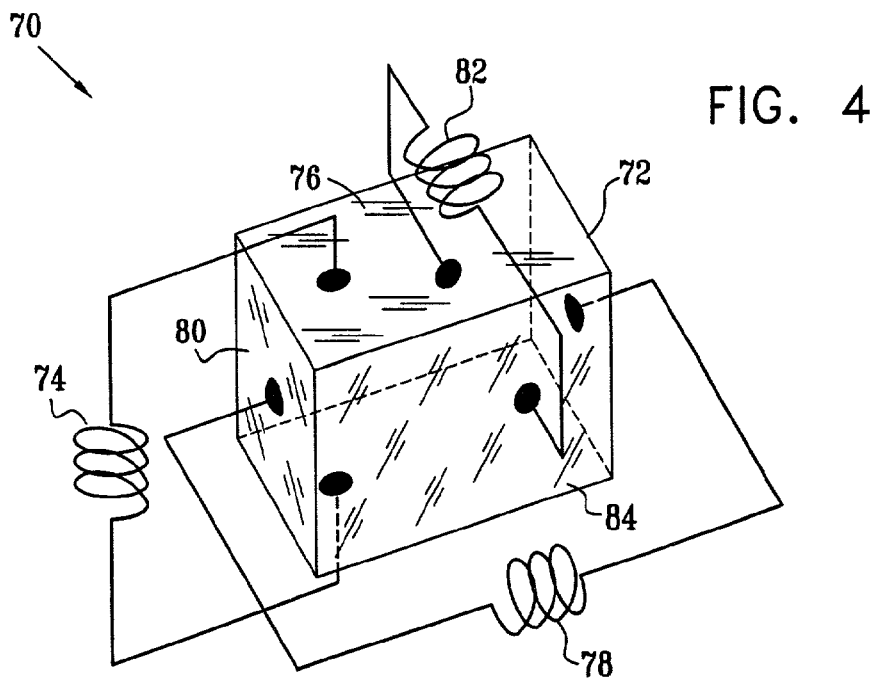
FIG. 4 is a schematic pictorial illustration of a piezoelectric tag, in accordance with a preferred embodiment of the present invention.

FIG. 4 is a schematic illustration of a tag 70, which comprises a polarized piezoelectric crystal 72, in accordance with a preferred embodiment of the present invention. Inductors (or coils) 74, 78 and 82 are connected across crystal 72, each inductor contacting a respective face 76, 80, 84 and its opposing face on the other side of the crystal. When tag 70 is irradiated with ultrasound waves by any of acoustic generators 11, 13 and 15, crystal 72 vibrates, and the voltages thus created between its opposing faces cause currents to flow in the respective inductors. As a result, the inductors radiate electromagnetic fields, which are detected by RF detector 17.

Tag 70 is preferably configured so that its response to the incident ultrasound waves is anisotropic. Preferably, crystal 72 is polarized at the time of its fabrication, so that its voltage response to the mechanical stimulus of the waves differs for each of its axes. Further preferably, each of inductors 76, 80 and 84 forms a part of a resonant circuit, each with a different resonant frequency. (Typically, each inductor is selected to have a different inductance.) Then, in response to the incident ultrasound irradiation, each inductor emits electromagnetic radiation at its particular frequency, with a magnitude that varies as a function of the relative angular orientation of the tag with respect to the source of the ultrasound radiation. Thus, signal processor 30 can analyze the electromagnetic waves emitted by tag 70 in order to yield both the location and the complete angular orientation of the tag.

Alternatively, tag 70 may be irradiated by electromagnetic waves generated by RF radiators 40, 42, 44. The waves induce currents to flow in inductors 74, 78 and 82, causing voltages to develop between the respective faces of crystal 72. As a result, the crystal vibrates, emitting ultrasonic waves, which are detected by acoustic detectors 34, 36, 38. Preferably, the inductors comprise coils with a large numbers of turns, so that high enough voltages are applied to the faces of the crystal to cause substantial vibrations. A voltage doubler circuit, as is known in the art, may also be used. If each of the inductors has a different frequency response, as described above, the variation of the emitted ultrasonic waves as a function of RF excitation frequency can be used by processor 30 to determine both the position and the orientation of tag 70.

Figure 5A:
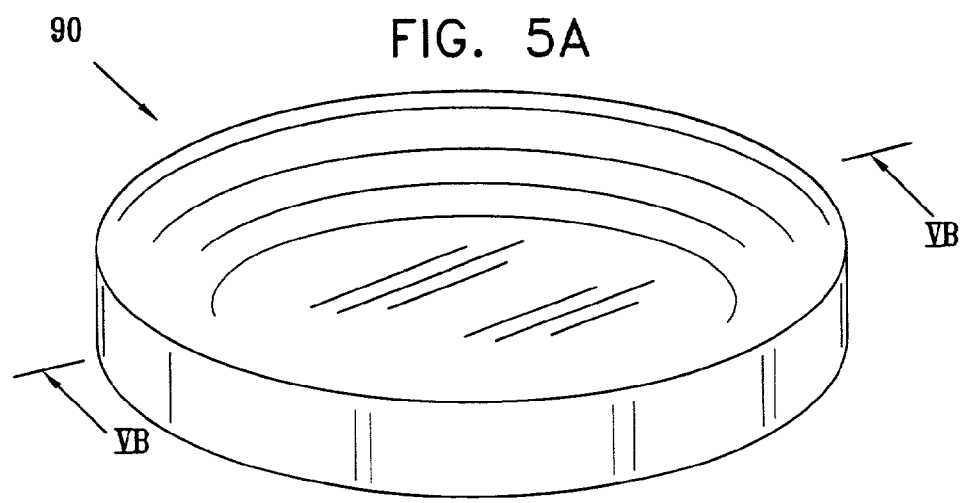
FIG. 5A is a schematic pictorial illustration of a magnetoacoustic tag, in accordance with a preferred embodiment of the present invention.
Figure 5B:
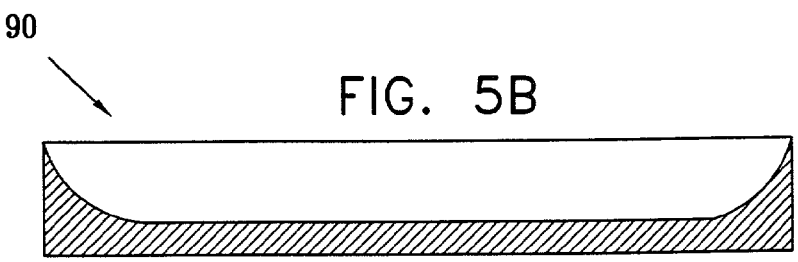
FIG. 5B is a schematic, cross-sectional view of the tag of FIG. 5A, taken along a line marked VB-VB.

FIGS. 5A and 5B schematically illustrate a tag 90 comprising a magnetoacoustic transducer, in accordance with a preferred embodiment of the present invention. FIG. 5A is a pictorial illustration, while FIG. 5B is a cross-sectional illustration, taken along line VB-VB in FIG. 5A. Tag 90 preferably comprises a magnetostrictive material, as is known in the art, such as Terfenol-D.

RF radiators 40, 42, 44 transmit electromagnetic radiation towards tag 90, preferably in the range of about 100-1000 kHz. The time-varying magnetic field of the radiation at the tag causes the tag to expand and contract, so that some of the electromagnetic energy is converted into mechanical vibrations. As a result, tag 90 emits ultrasound waves, typically at the frequency of the exciting magnetic field. These ultrasound waves are sensed by acoustic detectors 34, 36 and 38, and the resultant signals are analyzed by signal processor 30 to determine the location of the tag by triangulation.

Alternatively or additionally, acoustic generators 11, 13, 15 transmit ultrasound waves at tag 90, causing the tag to vibrate. As a result of the vibration, tag 90 generates an electromagnetic wave having a frequency determined by the properties of the transducer and by the frequency of the exciting ultrasound waves. The emitted electromagnetic wave is detected by RF detector 17.

Preferably, tag 90 is asymmetrical, and is shaped so that its vibrational frequency response is anisotropic. As a result, both the response of the tag to incident ultrasound waves (when the tag is excited by acoustic irradiation) and the pattern of emitted ultrasound waves (when the tag is excited by RF irradiation) vary as a function of the orientation angle of the tag. The spatial variation sensed by the RF or acoustic detectors can then be used to determine both the position and the orientation of tag 90, as described above.

Optionally, tag 90 is shaped so as to concentrate the emitted ultrasound or electromagnetic radiation in a particular direction, or at a particular location, with respect to the tag. For example, the tag may be plano-concave (as shown), causing the emitted radiation to be focused generally to a point outside the patient's body. An array of detectors, suitably positioned, can be used to determine the location of that focal point, and, consequently, the location and orientation of the tag within the patient's body. As a further option, several such shaped transducers may be included in a single tag. The ultrasound waves emitted by tag 90 may also be used for imaging, or to analyze properties of tissue in which the tag is placed.

Alternative, useful shapes for tag 90, suitable for enabling identification of the orientation of the tag, will be apparent to those skilled in the art. Cylindrical and disk shapes are particularly useful in generating directional ultrasonic pulses.

In a further embodiment of the present invention, not shown in the figures, a passive tag comprises a tunnel diode coupled to a resonant circuit. Circuits of this type and their use as passive transponders are described in detail in the above-mentioned U.S. Pat. No. 6,053,873. The circuit is excited by an electromagnetic wave generated one or more of radiators 40, 42, 44 at a first frequency (f1), and emits an electromagnetic wave of another frequency (f2). Tunnel diodes are particularly well suited for this purpose, because the characteristic I-V curve of a tunnel diode includes a portion in which the diode demonstrates "negative" resistance, i.e., as the voltage applied across the diode decreases, the current through the diode increases, causing oscillations to occur in the circuit. The oscillation frequency (f2) differs from the normal resonant frequency of the circuit because of the effective capacitance of the tunnel diode. Typically, frequency f2 differs from the excitation frequency f1 by about 10%-40%. For example, an excitation frequency f1 of 88 MHz may yield a waveform (detectable by the external apparatus) having a frequency f2 of 120 MHz.

Triangulation of the power of the electromagnetic wave emitted by the circuit yields the location of the tag. Typically, three or more RF detectors at respective sites are used for this purpose. The angular position of the tag can also be determined, at least in part, based on the angular position of the inductor in the resonant circuit. Optionally, the tag comprises multiple resonant circuits with mutually-orthogonal inductors, in order to allow more precise determination of the angular orientation of the tag.

It will be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for determining the position of an object within a body of a subject, comprising:
   at least one acoustic wave generator, adapted to direct a first acoustic wave toward the body at a first frequency;
   an acoustic tag adapted to be fixed to the object, the tag being wireless and comprising a shell defining a cavity therein and a medium contained within the shell, such that responsive to incidence thereon of the first acoustic wave, the tag emits a second acoustic wave at a second frequency, different from the first frequency;
   one or more detectors, adapted to detect the second acoustic wave and to generate signals responsive thereto; and
   a signal processor, coupled to process the signals so as to determine six-dimensional position and orientation coordinates of the object in the body.

2. Apparatus according to claim 1, wherein the tag has an axis and is constructed so that responsive to incidence thereon of the first acoustic wave, the tag emits the second acoustic wave at the second frequency with a first pattern of intensity variation relative to the axis, and a third acoustic wave at a third frequency, different from the first and second frequencies, with a second pattern of intensity variation relative to the axis, and wherein responsive to detection of the second and third acoustic waves by the one or more detectors, the signal processor is adapted to determine an angular orientation of the object responsive to a difference between the first and second patterns.

3. Apparatus for determining the position of an object within a body of a subject, comprising:
   at least one acoustic wave generator, adapted to direct acoustic waves toward the body over a range of frequencies, including at least first and second frequencies;
   an acoustic tag adapted to be fixed to the object, the tag being wireless and constructed so as to reflect the acoustic waves at the first frequency with a first spatial pattern of intensity variation, and to reflect the acoustic waves at the second frequency with a second spatial pattern of intensity variation;
   one or more detectors, adapted to detect the reflected acoustic waves and to generate signals responsive thereto; and
   a signal processor, coupled to process the signals so as to determine six-dimensional position and orientation coordinates of the object in the body responsive to a difference between the first and second spatial patterns.

4. Apparatus according to claim 3, wherein the tag has an axis, and wherein the tag is constructed so that in the first spatial pattern, the acoustic waves are reflected predominantly in a first direction relative to the axis, while in the second spatial pattern, the acoustic waves are reflected predominantly in a second direction relative to the axis, different from the first direction.

5. Apparatus for determining the position of an object within a body of a subject, comprising:
   at least one acoustic wave generator, adapted to direct acoustic waves toward the body;
   a transducer adapted to be fixed to the object, the transducer being wireless and constructed to emit electromagnetic radiation responsive to the acoustic waves with a response that varies depending on an orientation angle of the transducer relative to the at least one acoustic wave generator;
   one or more detectors, adapted to detect the electromagnetic radiation emitted by the transducer and to generate signals responsive thereto; and
   a signal processor, coupled to process the signals so as to determine six-dimensional position and orientation coordinates of the object in the body.

6. Apparatus according to claim 5, wherein the transducer comprises a piezoelectric crystal, which is polarized so as to respond anisotropically to the acoustic waves.

7. Apparatus according to claim 6, wherein the piezoelectric crystal has multiple opposing faces, and wherein the transducer further comprises a plurality of resonant circuit elements having different, respective resonant frequencies, the circuit elements being coupled between respective pairs of the faces of the crystal so as to emit the electromagnetic radiation at the different resonant frequencies with respective amplitudes that vary responsive to the orientation angle of the transducer.

8. Apparatus according to claim 7, wherein the circuit elements comprise coils having different, respective values of inductance.

9. Apparatus according to claim 5, wherein the transducer comprises a magnetostrictive element, which is shaped so as to respond anisotropically to the acoustic waves.

10. Apparatus according to claim 9, wherein the magnetostrictive element is shaped to as to focus the electromagnetic radiation that it emits.

11. Apparatus for determining the position of an object within a body of a subject, comprising:
    at least one field generator, adapted to generate an electromagnetic field within the body;

a transducer adapted to be fixed to the object, the transducer being wireless and constructed to emit acoustic waves responsive to the electromagnetic field;

one or more acoustic detectors, adapted to detect the acoustic waves emitted by the transducer and to generate signals responsive thereto; and a signal processor, coupled to process the signals so as to determine six-dimensional position and orientation coordinates of the object in the body.

12. Apparatus according to claim 11, wherein the transducer comprises a piezoelectric crystal, which is polarized so as to respond anisotropically to the electromagnetic field.

13. Apparatus according to claim 12, wherein the piezoelectric crystal has multiple opposing faces, and wherein the transducer further comprises a plurality of resonant circuit elements having different, respective resonant frequencies, the circuit elements being coupled between respective pairs of the faces of the crystal so as to cause the crystal to emit the acoustic waves at the different resonant frequencies with respective amplitudes that vary responsive to the orientation angle of the transducer.

14. Apparatus according to claim 13, wherein the circuit elements comprise coils having different, respective values of inductance.

15. Apparatus according to claim 11, wherein the transducer comprises a magnetoacoustic transducer.

16. Apparatus according to claim 15, wherein the transducer comprises a magnetostrictive material.

17. Apparatus according to claim 15, wherein the magnetoacoustic transducer is shaped so as to respond anisotropically to the electromagnetic field, so that the acoustic waves emitted thereby vary as a function of an orientation angle of the transducer relative to the at least one field generator, and wherein the signal processor is adapted to determine the orientation angle of the object responsive to the signals.

18. Apparatus according to claim 17, wherein the magnetoacoustic element is shaped to as to focus the electromagnetic radiation that it emits.

19. A method for determining the position of an object within a body of a subject, comprising:

fixing an acoustic tag to the object, the tag being wireless and comprising a shell defining a cavity therein and a medium contained within the shell, such that responsive to incidence thereon of a first acoustic wave at a first frequency, the tag emits a second acoustic wave at a second frequency, different from the first frequency;

inserting the object into the body of the subject;

directing the first acoustic wave toward the body at the first frequency, causing the tag to emit the second acoustic wave at the second frequency;

detecting the second acoustic wave and generating signals responsive thereto; and processing the signals so as to determine six-dimensional position and orientation coordinates of the object in the body.

20. A method according to claim 19, wherein the tag has an axis and is constructed so that responsive to incidence thereon of the first acoustic wave, the tag emits the second acoustic wave at the second frequency with a first pattern of intensity variation relative to the axis, and a third acoustic wave at a third frequency, different from the first and second frequencies, with a second pattern of intensity variation relative to the axis, and comprising detecting the third acoustic wave and generating the signals responsive thereto, wherein processing the signals comprises determining an angular orientation of the object responsive to a difference between the first and second patterns.

21. A method for determining the position of an object within a body of a subject, comprising:

fixing an acoustic tag to the object, the tag being wireless and constructed so as to reflect acoustic waves at a first frequency with a first spatial pattern of intensity variation, and to reflect acoustic waves at a second frequency with a second spatial pattern of intensity variation;

inserting the object into the body of the subject;

directing the acoustic waves toward the body over a range of frequencies, including at least the first and second frequencies;

detecting the reflected acoustic waves and generating signals responsive thereto; and processing the signals so as to determine six-dimensional position and orientation coordinates of the object in the body responsive to a difference between the first and second spatial patterns.

22. A method according to claim 21, wherein the tag has an axis, and wherein the tag is constructed so that in the first spatial pattern, the acoustic waves are reflected predominantly in a first direction relative to the axis, while in the second spatial pattern, the acoustic waves are reflected predominantly in a second direction relative to the axis, different from the first direction.

23. A method for determining the position of an object within a body of a subject, comprising:

fixing a transducer to the object, the transducer being wireless and configured to emit electromagnetic radiation responsive to acoustic waves incident thereon with a response that varies depending on an orientation angle of the transducer relative to a source of the acoustic waves;

inserting the object into the body of the subject;

directing the acoustic waves toward the body;

detecting the electromagnetic radiation emitted by the transducer responsive to the acoustic waves, and generating signals responsive thereto; and processing the signals so as to determine six-dimensional position and orientation coordinates of the object in the body.

24. A method according to claim 23, wherein the transducer comprises a piezoelectric crystal, which is polarized so as to respond anisotropically to the acoustic waves.

25. A method according to claim 24, wherein the piezoelectric crystal has multiple opposing faces, and wherein the transducer further comprises a plurality of resonant circuit elements having different, respective resonant frequencies, the circuit elements being coupled between respective pairs of the faces of the crystal so as to emit the electromagnetic radiation at the different resonant frequencies with respective amplitudes that vary responsive to the orientation angle of the transducer.

26. A method according to claim 25, wherein the circuit elements comprise coils having different, respective values of inductance.

27. A method according to claim 23, wherein processing the signals further comprises determining position coordinates of the object responsive to the signals.

28. A method according to claim 23, wherein the transducer comprises a magnetostrictive element, which is shaped so as to respond anisotropically to the acoustic waves.

29. A method according to claim 28, wherein the magnetostrictive element is shaped to as to focus the electromagnetic radiation that it emits.

30. A method for determining the position of an object within a body of a subject, comprising:

fixing a transducer to the object, the transducer being wireless and configured to emit acoustic waves responsive to an electromagnetic field that is incident thereon;
inserting the object into the body of the subject;
generating the electromagnetic field within the body;
detecting the acoustic waves emitted by the transducer and generating signals responsive thereto; and processing the signals so as to determine six-dimensional position and orientation coordinates of the object in the body.

31. A method according to claim 30, wherein the transducer comprises a piezoelectric crystal, which is polarized so as to respond anisotropically to the electromagnetic field.

32. A method according to claim 31, wherein the piezoelectric crystal has multiple opposing faces, and wherein the transducer further comprises a plurality of resonant circuit elements having different, respective resonant frequencies, the circuit elements being coupled between respective pairs of the faces of the crystal so as to cause the crystal to emit the acoustic waves at the different resonant frequencies with respective amplitudes that vary responsive to the orientation angle of the transducer.

33. A method according to claim 32, wherein the circuit elements comprise coils having different, respective values of inductance.

34. A method according to claim 30, wherein the transducer comprises a magnetoacoustic transducer.

35. A method according to claim 31, wherein the transducer comprises a magnetostrictive material.

36. A method according to claim 31, wherein the magnetoacoustic transducer is shaped so as to respond anisotropically to the electromagnetic field, so that the acoustic waves emitted thereby vary as a function of an orientation angle of the transducer relative to the at least one field generator, and wherein processing the signals comprises determining the orientation angle of the object responsive to the signals.

37. A method according to claim 36, wherein the magnetoacoustic element is shaped to as to focus the electromagnetic radiation that it emits.

* * * * *